United States Patent

Okitsu

[11] Patent Number: 4,738,977
[45] Date of Patent: Apr. 19, 1988

[54] 2-PYRIDYLACETIC ACID DERIVATIVES, PHARMACEUTICAL COMPOSITION CONTAINING THE SAME AND THEIR USE IN TREATING ULCERS

[75] Inventor: Mitsuhito Okitsu, Osaka, Japan

[73] Assignee: Suntory Limited, Osaka, Japan

[21] Appl. No.: 925,175

[22] Filed: Oct. 31, 1986

[30] Foreign Application Priority Data

Nov. 8, 1985 [JP] Japan .................. 60-248970

[51] Int. Cl.$^4$ .................. C07D 213/83; A61K 31/44
[52] U.S. Cl. .................. 514/357; 514/318; 514/336; 514/343; 546/193; 546/194; 546/268; 546/281; 546/331
[58] Field of Search .................. 546/331; 514/357

[56] References Cited

U.S. PATENT DOCUMENTS 4,272,534  6/1981  Aloup .................. 514/229

OTHER PUBLICATIONS

Smith, The Chemistry of Open-Chain Organic Nitrogen Compounds, vol. I, p. 29, Benjamin Pub. 1965.
March, Advanced Organic Chemistry, Reactions, Mechanisms and Structure, Second Edition, p. 386, McGraw-Hill Pub. 1977.

Primary Examiner—Alan L. Rotman
Attorney, Agent, or Firm—Burns, Doane, Swecker & Mathis

[57] ABSTRACT

A 2-pyridylacetic acid derivative having the formula (I):

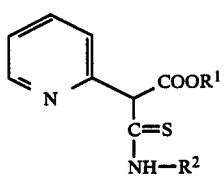

wherein $R^1$ represents an alkyl having 1 to 15 carbon atoms, an alkenyl having 5 to 20 carbon atoms or an aralkyl having 7 to 15 carbon atoms; $R^2$ represents hydrogen, a linear or cyclic alkyl, a hydroxyalkyl group, an alkenyl, an aryl, an aralkyl or a group—$(CH_2)_n$—A, where n represents an integer of 0 to 3 and A represents a nitrogen-containing heterocyclic group which may be substituted with an alkyl having 1 to 10 carbon atoms or an aralkyl having 7 to 10 carbon atoms and a pharmacologically acceptable acid addition salt thereof.

This compound has both effects of the inhibition of gastric acid and the protection of gastric mucosa, which is low in toxicity.

Accordingly, it is useful as a therapeutical agent for peptic ulcer disease.

26 Claims, No Drawings

2-PYRIDYLACETIC ACID DERIVATIVES, PHARMACEUTICAL COMPOSITION CONTAINING THE SAME AND THEIR USE IN TREATING ULCERS

BACKGROUND OF THE INVENTION

1. Field of the Invention

The present invention relates to a 2pyridylacetic acid having the formula (I):

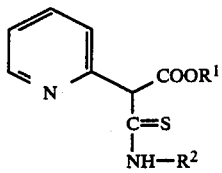

(I)

wherein $R^1$ represents an alkyl having 1 to 15 carbon atoms, an alkenyl having 5 to 20 carbon atoms or an aralkyl having 7 to 15 carbon atoms; $R^2$ represents hydrogen, a linear or cyclic alkyl preferably having 1 to 10 carbon atoms, a hydroxyalkyl preferably having 2 to 6 carbon atoms, an alkenyl preferably having 3 to 6 carbon atoms, an aryl preferably having 6 to 10 carbon atoms, an aralkyl preferably having 7 to 15 carbon atoms or a group—$(CH_2)_n$—A, where n represents an integer of 0 to 3 and A represents a nitrogen-containing hterocyclic group which may be substituted with an alkyl having 1 to 10 carbon atoms or an aralkyl having 7 to 10 carbon atoms, a process for preparation thereof and a pharmaceutical composition or agent containing the same. More specifically, the 2-pyridylacetic acid derivatives and its pharmacologically acceptable acid addition salts are novel compounds useful as therapeutical agents for peptic ulcers, since they have the effect of inhibiting attacking factors of peptic ulcer and the effect of potentiating defending factors and also have a low toxicity.

2. Description of the Related Art

The etiology of peptic ulcer has been discussed in terms of an imbalance between aggressive and defensive factors, but the factors which increase the resistance of tissue have not yet been clarified. Accordingly, the maximum "no acid, no ulcer" remains still true, and under the present situation, the therapy target of peptic ulcers is still directed to a control of gastric acid.

In the recent years, potent inhibitors of gastric acid secretion such as histamine $H_2$ receptor antagonist (cimetidine, ranitidine, famotidine) and anticholinergics of gastric acid (pirenzepine) were introduced to therapeutics of gastric and duodenal ulcer patients.

However, these are not sufficient for preventing worsening or recurrence of ulcer.

As mentioned above, a sufficient effect cannot be obtained in the therapy of an ulcer only by the use of a drug which can prevent the generation of an ulcer, namely inhibit aggressive factors. Accordingly, under the present situation, a drug inhibiting aggressive factors and a protective drug for gastric mucosa are respectively selected or used in combinations of both types as the ulcer therapeutical agent, depending on the conditions of the disease. Although some compounds stated to have both such effects have been proposed, in practice these proved to have a weak inhibiting acid secretion, and to primarily have a protective effect for gastric mucosa.

SUMMARY OF THE INVENTION

As described above, the development of a potent anti-peptic ulcer drug well balanced in both the actions of inhibition of aggressive factors and protection of gastric mucosa is strongly desired. Furthermore, it is also important that such a drug should have a very low toxicity and a minimum of side effects as a drug for peptic ulcer disease.

Accordingly, the object of the present invention is to provide a novel compound, in which the above-mentioned activities are well balanced, and having a low toxicity.

Other objects and advantages of the present invention will be apparent from the following description.

In accordance with the present invention, there is provided 2-pyridylacetic acid derivative having the above-mentioned formula (I) and a pharmacologically acceptable acid addition salt thereof.

In accordance with the present invention, there is also provided a process for preparing the compound having the formula (I) and a pharmacologically acceptable acid addition salt thereof which comprises reacting an addition product having the formula (III):

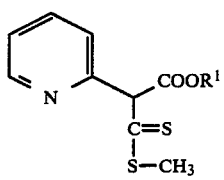

(III)

wherein $R^1$ is as defined above; with ammonia or an amine represented by the formula (IV):

$$R^2-NH_2 \qquad (IV)$$

wherein $R^2$ is as defined above, followed by treatment with a pharmacologically acceptable acid, if desired.

In accordance with the present invention, there is also provided a peptic ulcer therapeutical agent comprising the 2-pyridylacetic acid derivative having the formula (I) and/or a pharmacologically acceptable acid addition salt thereof as the active ingredient.

DESCRIPTION OF THE PREFERRED EMBODIMENTS

The novel compound 2-pyridylacetic acid derivative having the above-mentioned formula (I) and its pharmacologically acceptable acid addition salt according to the present invention has a protecting action of gastric mucosa together with an effect of inhibiting gastric acid secretion, and has a low toxicity, and therefore, is a useful substance which can be used for the therapy of a peptic ulcer.

The compound having the above-mentioned formula (I) of the present invention can be prepared as follows:

That is, a 2-pyridylacetic acid ester having the formula (II):

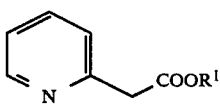

wherein R¹ is as defined above, is allowed to react with carbon disulfide in an organic solvent in the presence of a base at a temperature of −78° C. to 0° C. The reaction is completed within several minutes to several tens of minutes. After completion of the reaction, methyl iodide is added and stirring is continued for several hours, whereby an addition product having the formula (III):

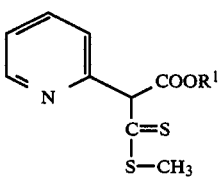

wherein R¹ is as defined above, can be obtained.

The solvent usable in the above reaction, may include, for example, an ether such as tetrahydrofuran, ether, dimethoxyethane or dioxane, or an aromatic hydrocarbon such as benzene, toluene or xylene, or dimethyl sulfoxide. Alternatively, the base usable in the above reaction may preferably include an alkyl lithium reagent, sodium amide, sodium hydride, potassium hydride, potassium t-butoxide, a sodium alcoholate, a potassium alcoholate, metallic sodium, and the like.

The amount of the base to be used in the above-mentioned reaction is not particularly limited, but may be, for example, 1 to 1.2 equivalent relative to the above compound (II).

The thus-obtained addition product having the formula (III) can be purified by a purification method conventionally employed, for example, chromatography, recrystallization or distillation.

When the above compound (III) is allowed to react with ammonia or an amine having the formula (IV):

$$R^2-NH_2 \quad (IV)$$

wherein R² is as defined above, in water and an organic solvent, or in an organic solvent, for 10 to 30 hours, the present compound can be obtained. The solvent usable in this reaction is not particularly limited, unless the reaction is adversely affected, but preferably, for example, water, an alcoholic solvent, a chlorine type solvent, an aromatic hydrocarbon solvent, an ether solvent, or an acetic acid ester solvent is used.

After completion of the reaction, the desired compound can be purified by, for example, recrystallization, column chromatography, or alternatively it can be treated with a pharmacologically acceptable acid and converted into an acid addition salt, which, in turn, can be purified by recrystallization or chromatography.

The acids usable for the preparation of the acid addition salts of the above 2-pyridylacetic acid derivative according to the present invention may include, for example, inorganic acids such as hydrochloric acid, hydrobromic acid, sulfuric acid, phosphoric acid, perchoric acid, and the like, and organic acids such as acetic acid, oxalic acid, citric acid, lactic acid, maleic acid, succinic acid, fumaric acid, tartaric acid, gluconic acid, mandelic acid, methanesulfonic acid, and the like.

Another process for preparing the 2-pyridylacetic acid derivative according to the present invention comprises dissolving a compound having the above formula (II) in an organic solvent and treating it with a base at a temperature of 0° C. or lower. Examples of such organic solvents are, preferably, ether solvents and aromatic hydrocarbon solvents. The amount of the base used in the above reaction is not particularly limited, but is preferably used at 1.0 to 1.2 equivalent relative to the compound of the above formula (II). Examples of such bases are, preferably, sodium hydride, a sodium alkoxide, a potassium alkoxide, sodium amide, n-butyllithium, and metallic sodium.

In the next step, an isothiocyanate having the formula (V):

$$S=C=N-R^3 \quad (V)$$

wherein R³ represents a linear or straight chain or cyclic alkyl group, an alkenyl group, an aryl group or an aralkyl group, is added to the above-mentioned reaction mixture, whereby a compound according to the present invention having the formula (Ia):

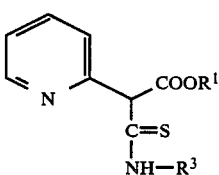

wherein R¹ and R³ are as defined above, can be obtained.

The novel 2-pyridylacetic acid having the above formula (I) according to the present invention may be administered as it is, but can be formed in various kinds of dosage forms by utilizing known preparation methods. For example, for oral administration, it can be generally formed into preparations such as tablets, powders, granules, capsules, syrup, and the like, or for parenteral administration, can be injected or filled in suppositories, and the like. In either case, preparations with various forms can be obtained by mixing with known liquid or solid excipients or carriers conventionally used in the preparation.

Examples of such exicipients or carriers may include polyvinyl pyrrolidone, gum arabic, gelatin, sorbitol, tragacanth, magnesium stearate, talc, polyethylene glycol, polyvinyl alcohol, silica, lactose, crystalline cellulose, sugar, starch, calcium phosphate, vegetable oil, carboxymethyl cellulose calcium, sodium lauryl sulfate, water, ethanol, glycerine, mannitol, syrup, and the like.

The peptic ulcer therapeutical agent of the present invention can contain the compound having the formula (I), or a pharmacologically acceptable acid addition salt thereof, in an effective amount.

The effective amount of the peptic ulcer therapeutical agent of the present invention to be administered may be varied depending on the condition and the age of the patient to be treated, the administration route, the dosage form, the number of administrations, and the like, but may be, for example, generally within the scope of from about 50 to 2,000 mg, preferably from 100 to 1,000 mg, for a human adult per day.

EXAMPLES

The present invention will now be further illustrated by, but is by no means limited to, the following Examples.

The compounds having the above formula (I) of the present invention were synthesized according to the two methods as described below. The method incorporating the formula (III) is called method B, and the method for obtaining the compound (Ia) of the present invention by allowing an isothiocyanate to react directly with the formula (II) is called method A.

EXAMPLE 1

Synthesis of ethyl 2-methylthiocarbamoyl-2-(2-pyridyl)acetate:

Synthesis according to method A

A 10.0 g (60.5 mmole) amount of ethyl 2-pyridylacetate was dissolved in 150 ml of dry tetrahydrofuran, and to the resultant solution were added, under a nitrogen gas stream and at a temperature of $-78°$ C. to $0°$ C., 1.1 equivalent of n-butyl lithium solution in hexane or 1.1 equivalent of powdery sodium amide, followed by stirring for 15 to 30 minutes.

To the resultant solution was added 4.87 g (66.6 mmole) of methylisothiocyanate, and the mixture was stirred at room temperature for 2 hours. Water was then added to the reaction mixture, and the mixture was extracted with chloroform.

The organic layer was then washed with water, and dried over anhydrous magnesium sulfate.

The residue obtained by evaporation of the solvent was subjected to column chromatography on silica gel to obtain 9.81 g of the desired compound as a yellow oil (yield 68%).

Synthesis according to method B

A 5.00 g (30.3 mmole) amount of ethyl 2-pyridiylacetate was dissolved in 50 ml of dry tetrahydrofuran, and to the resultant solution was added, under a nitrogen stream at $-78°$ C., 1.25 equivalent of n-butyl lithium solution in hexane. After 15 minutes, 2.88 g (37.8 mmole) of carbon disulfide was added, and further, after stirring for 15 minutes, 5.37 g (37.8 mmcle) of methyl iodide was added, followed by stirring at room temperature for 2 hours.

Water was added to the reaction mixture obtained above, and the mixture was extracted with chloroform. The organic layer was then washed with water, followed by drying over anhydrous magnesium sulfate.

The residue obtained by evaporation of the solvent was subjected to column chromatography on silica gel to obtain ethyl 2-dithiomethoxycarbonyl-2-(2-pyridyl)acetate as a yellow oil.

This was dissolved in 30 ml of ethanol and 1.0 equivalent of methylamine solution in ethanol was added at room temperature, and the mixture was further stirred for 1 hour. The residue obtained by concentration was subjected to column chromatography on silica gel to obtain 3.70 g of the desired compound (yield 51%).

EXAMPLES 2 to 16

The following compounds were synthesized in the same manner as in method A in Example 1.

The physical properties of these compounds are summarized in Table 1.

EXAMPLE 2

Ethyl 2-ethylthiocarbamoyl-2-(2-pyridyl)acetate

EXAMPLE 3

Ethyl 2-allylthiocarbamoyl-2-(2-pyridyl)acetate

EXAMPLE 4

Ethyl 2-cyclohexylthiocarbamoyl-2-(2-pyridyl)acetate

EXAMPLE 5

Ethyl 2-benzylthiocarbamoyl-2-(2-pyridyl)acetate

EXAMPLE 6

Ethyl 2-phenylthiocarbamoyl-2-(2-pyridyl)acetate

EXAMPLE 7

Ethyl 2-adamantylthiocarbamoyl-2-(2-pyridyl)acetate

EXAMPLE 8

Benzyl 2-methylthiocarbamoyl-2-(2-pyridyl)acetate

EXAMPLE 9

Prenyl 2-methylthiocarbamoyl-2-(2-pyridyl)acetate

EXAMPLE 10

Prenyl 2-allylthiocarbamoyl-2-(2-pyridyl)acetate

EXAMPLE 11

Prenyl 2-phenylthiocarbamoyl-2-(2-pyridyl)acetate

EXAMPLE 12

Geranyl 2-methylthiocarbamoyl-2-(2-pyridyl)acetate

EXAMPLE 13

Geranyl 2-allylthiocarbamoyl-2-(2-pyridyl)acetate

EXAMPLE 14

Geranyl 2-phenylthiocarbamoyl-2-(2-pyridyl)acetate

EXAMPLE 15

Farnesyl 2-methylthiocarbamoyl-2-(2-pyridyl)acetate

EXAMPLE 16 t-Butyl 2-methylthiocarbamoyl-2-(2-pyridyl)acetate

TABLE 1

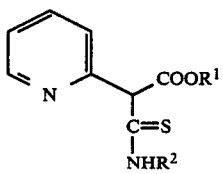

| Example | R¹ | R² | m.p. (°C.) | IR spectrum (cm⁻¹) | NMR spectrum (CDCl₃, δ) | Preparation method, yield (%) |
|---|---|---|---|---|---|---|
| 1 | C₂H₅ | —CH₃ | oil | 3260, 1730, 1540, 1290, 1150, 740 (film) | 1.21 (3H, t, J=7.2 Hz), 3.22 (3H, d, J=4.6 Hz), 4.08–4.31 (2H, m), 5.40 (1H, s), 7.25–7.30 (1H, m), 7.45 (1H, d, J=7.6 Hz), 7.72 (1H, t, d, J=7.6 Hz, J=2.0 Hz), 8.56 (1H, br.d, J=3.9 Hz), 10.19 (1H, br.s) | A 68 B 51 |
| 2 | C₂H₅ | —C₂H₅ | oil | 3250, 2995, 1735, 1540, 1290, 1160, 750 (film) | 1.21 (3H, t, J=7.2 Hz), 1.29 (3H, t, J=7.3 Hz), 3.57–3.85 (2H, m), 4.10–4.30 (2H, m), 5.36 (1H, s), 7.25–7.30 (1H, m), 7.45 (1H, d, J=7.9 Hz), 7.57 (1H, d, J=3.9 Hz), 10.04 (1H, br.s) | 59 |
| 3 | C₂H₅ | —CH₂CH=CH₂ | 49–50 (yellow prism) | 3260, 2980, 1740, 1540, 1435, 1290, 1160, 750 (KBr) | 1.21 (3H, t, J=7.3 Hz), 4.10–4.45 (4H, m), 5.18–5.33 (2H, m), 5.40 (1H, s), 5.82–6.00 (1H, m), 7.25–7.28 (1H, m), 7.45 (1H, d, J=7.9 Hz), 7.72 (1H, t, d, J=7.9 Hz, J=2.0 Hz), 8.57 (1H, d, J=3.9 Hz), 10.21 (1H, br.s) | 42 |
| 4 | C₂H₅ | cyclohexyl | oil | 3240, 2930, 2850, 1740, 1545, 1430, 1290, 750 (film) | 1.21 (3H, t, J=7.3 Hz), 1.20–2.20 (10H, m), 4.10–4.22 (2H, m), 4.30–4.41 (1H, m), 5.18 (1H, s), 7.23–7.32 (1H, m), 7.43 (1H, d, J=7.9 Hz), 7.73 (1H, t.d, J=7.9 Hz, J=2.0 Hz), 8.56 (1H, d, J=3.9 Hz), 10.08 (1H, br.s) | 84 |
| 5 | C₂H₅ | —CH₂—C₆H₅ | 98–101 (colorless needle) | 3250, 1735, 1540, 1260, 1020, 740 (KBr) | 1.20 (3H, t, J=7.3 Hz), 4.10–4.24 (2H, m), 4.76–5.02 (2H, m), 5.45 (1H, s), 7.24–7.33 (6H, m), 7.47 (1H, d, J=7.9 Hz), 7.72 (1H, t.d, J=7.9 Hz, J=2.0 Hz), 8.50 (1H, d, J=5.6 Hz), 10.43 (1H, br.s) | 66 |
| 6 | C₂H₅ | —C₆H₅ | oil | 3250, 2960, 1730, 1580, 1420, 1280, 1020, 745 (film) | 1.24 (3H, t, J=7.2 Hz), 4.14–4.28 (2H, m), 5.47 (1H, s), 7.21–7.51 (5H, m), 7.73–7.83 (3H, m), 8.62 (1H, d, J=4.0 Hz), 11.97 (1H, br.s) | 72 |
| 7 | C₂H₅ | adamantyl | oil | 3250, 2900, 1730, 1560, 1440, 1160, 745 (film) | 1.21 (3H, t, J=7.3 Hz), 1.62–2.40 (15H, m), 4.06–4.30 (2H, m), 5.20 (1H, s), 7.23–7.30 (1H, m), 7.43 (1H, d, J=7.9 Hz), 7.71 (1H, t.d, J=7.9 Hz, J=3.9 Hz), 8.55 (1H, d, J=3.9 Hz), 9.87 (1H, br.s) | 16 |
| 8 | CH₂—C₆H₅ | —CH₃ | oil | 3250, 1730, 1550, 1460, 1380, 1290, 1150, 740 (film) | 3.18 (3H, d, J=4.6 Hz), 4.24 (2H, s), 5.46 (1H, s), 7.18–7.47 (7H, m), 7.71 (1H, t.d, J=7.9 Hz, J=2.0 Hz), 8.53 (1H, d, J=3.9 Hz), 10.14 (1H, br.s) | 45 |
| 9 | (CH₃)₂C=CHCH₂- | —CH₃ | oil | 3250, 2950, 1735, 1545, 1380, 1150, 750 (film) | 1.63 (3H, s), 1.71 (3H, s), 3.22 (3H, d, J=4.9 Hz), 4.55–4.63 (2H, m), 5.25 (1H, m), 5.40 (1H, s), 7.24–7.29 (1H, m), 7.45 (1H, d, J=7.9 Hz), 7.71 (1H, t.d, J=7.9 Hz, J=2.0 Hz), 8.56 (1H, d, J=4.0 Hz), 10.13 (1H, br.s) | 84 |
| 10 | (CH₃)₂C=CHCH₂- | —CH₂CH=CH₂ | oil | 3240, 2950, 1730, 1530, 1430, 1280, 1180, 740 (film) | 1.62 (3H, s), 1.71 (3H, s), 4.23–4.44 (2H, m), 4.51–4.69 (2H, m), 5.16–5.30 (2H, m), 5.40 (1H, s) 5.84–5.98 (H, m), 7.25–7.30 (1H, m), 7.45 (1H, d, J=7.9 Hz), 7.71 (1H, t.d, J=7.9 Hz, J=2.0 Hz), 8.56 (1H, d, J=4.0 Hz), 10.18 (1H, br.s) | 61 |
| 11 | (CH₃)₂C=CHCH₂- | —C₆H₅ | oil | 3250, 2950, 1730, 1560, 1420, 1280, 1160, 750 (film) | 1.64 (3H, s), 1.72 (1H, s), 4.55–4.73 (2H, m), 5.29 (1H, br.t, J=8.6 Hz), 5.47 (1H, s), 7.21–7.51 (5H, m), 7.72–7.84 (3H, m), 8.62 (1H, d, J=4.0 Hz), 11.93 (1H, br.s) | 46 |

TABLE 1-continued

Structure: 2-pyridyl-CH(COOR¹)-C(=S)-NHR²

| Example | R¹ | R² | m.p. (°C.) | IR spectrum (cm⁻¹) | NMR spectrum (CDCl₃, δ) | Preparation method, yield (%) |
|---|---|---|---|---|---|---|
| 12 | geranyl (CH₃, CH₃, CH₃ with chain) | —CH₃ | oil | 3250, 2930, 1730, 1540, 1380, 1150, 1040, 740 (film) | 1.58 (3H, s), 1.62 (3H, s), 1.67 (3H, s), (2.00–2.12 (4H, m), 3,22 (3H, d, J=4.9 Hz), 4.58–4.65 (2H, m), 5.04 (1H, m), 5.24 (1H, m), 5.40 (1H, s), 7.24–7.29 (1H, m), 7.45 (1H, d, J=7.9 Hz), 7.71 (1H, t.d, J=7.9 Hz, J=2.0 Hz), 8.56 (1H, d, J=4.0 Hz), 10.15 (1H, br.s) | 56 |
| 13 | geranyl | —CH₂CH=CH₂ | oil | 3250, 2920, 1735, 1540, 1430, 1280, 1150, 750 (film) | 1.58 (3H, s), 1.62 (3H, s), 1.67 (3H, s), 1.97–2.12 (4H, m), 4.22–4.47 (2H, m), 4.55–4.72 (2H, m), 5.04 (1H, m), 5.18–5.40 (3H, m), 5.41 (1H, s), 5.84–5.97 (1H, m), 7.25–7.30 (1H, m), 7.45 (1H, d, J=7.9 Hz), 7.72 (1H, t.d, J=7.9 Hz), J=2.0 Hz), 8.56 (1H, d, J=4.0 Hz), 10.26 (1H, br.s) | 51 |
| 14 | geranyl | —C₆H₅ | oil | 3250, 2940, 1730, 1590, 1560, 1420, 1150, 1100, 750 (film) | 1.58 (3H, s), 1.64 (3H, s), 1.67 (3H, s), 1.96–2.14 (4H, m), 4.58–4.75 (2H, m), 5.04 (1H, br.s) 5.29 (1H, t, J=6.6 Hz), 5.46 (1H, s), 7.21–7.51 (5H, m), 7.72–7.84 (3H, m), 8.62 (1H, d, J=4.0 Hz), 11.94 (1H, br.s) | 60 |
| 15 | geranylgeranyl-like (CH₃, CH₃, CH₃) | —CH₃ | oil | 3300, 2930, 1730, 1540, 1450, 1380, 1280, 1150, 740 (film) | 1.60 (3H, s), 1.62 (3H, s), 1.68 (6H, s), 1.95–2.15 (8H, m), 3.22 (3H, d, J=4.6 Hz), 4.50–4.72 (2H, m), 5.02–5.18 (2H, m), 5.25 (1H, br.t), 5.4 (1H, s), 7.24–7.29 (1H,m), 7.45 (1H, d, J=7.9 Hz), 7.71 (1H, t.d, J=7.9 Hz, 2.0 Hz), 8.56 (1H, d, J=4.0 Hz), 10.16 (1H, br.s) | 74 |
| 16 | t-butyl (C(CH₃)₃) | —CH₃ | 102 (colorless prism) | 3300, 2980, 1720, 1560, 1140, 1040, 760 (KBr) | 1.38 (9H, s), 3.22 (3H, d, J=4.6 Hz), 5.31 (1H, s), 7.23–7.28 (1H, m), 7.42 (1H, d, J=7.9 Hz), 7171 (1H, t.d, J=7.9 Hz, J=2.0 Hz), 8.55 (1H, d, J=4.0 Hz), 10.20 (1H, br.s) | 79 |

EXAMPLE 17

Synthesis of geranyl 2-thiocarbamoyl-2-(2-pyridyl)acetate

A 16.5 g (60.4 mmole) amount of geranyl 2-pyridylacetate was dissolved in 150 ml of dry tetrahydrofuran and, to the resultant solution, 1.2 equivalent of n-butyl lithium solution in hexane was added under a nitrogen stream at −78° C.

After fifteen minutes, 5.52 g (72.4 mmole) of carbon disulfide was added at the same temperature, followed further by stirring for 15 minutes, and 10.28 g (72.4 mmol) of methyl iodide was then added.

After stirring at room temperature for 2 hours, water was added and the mixture was extracted with chloroform. The extract was washed with water, dried over anhydrous magnesium sulfate, and the solvent was evaporated to give a residue which was subjected to silica gel column chromatography to obtain geranyl 2-dithiomethoxycarbonyl-2-(pyridyl)acetate as a yellow oil.

This was dissolved in 20 ml of ethanol and 1.12 ml of a 28% aqueous ammonia containing 1.0 equivalent of ammonia was added to the solution, followed by stirring at room temperature for 15 hours.

After evaporation of the ethanol, the reaction mixture was diluted with water and extracted with chloroform. The extract was washed with water, dried over anhydrous magnesium sulfate, and the solvent was evaporated. The residue obtained was subjected to column chromatography on silica gel to obtain 9.83 g of the title compound (yield 49%).

EXAMPLES 18 to 27

Following method B in Example 1, compounds of the following Example numbers were synthesized in the same manner as in Example 17.

The physical data of these compounds are summarized in Table 2.

EXAMPLE 18

Prenyl 2-thiocarbamoyl-2-(2-pyridyl)acetate

EXAMPLE 19

Ethyl 2-propylthiocarbamoyl-2-(2-pyridyl)acetate

EXAMPLE 20

Ethyl 2-(3-hydroxypropyl)thiocarbamoyl-2(2-pyridyl)acetate

EXAMPLE 21

Ethyl 2- [(S)-2-methylbenzyl]thiocarbamoyl-2(2-pyridyl)acetate

EXAMPLE 22

Ethyl 2-[(R)-2-methylbenzyl]thiocarbamoyl-2(2-pyridyl)acetate

EXAMPLE 23

Ethyl 2-diphenylmethylthiocarbamoyl-2(2-pyridyl)acetate

EXAMPLE 24

Ethyl 2-(2-pyridyl)methylthiocarbamoyl-2-(2-pyridyl)acetate

EXAMPLE 25

Ethyl 2-[L4-(1-benzyl)piperidyl]thiocarbamoyl-2-(2-pyridyl)acetate

EXAMPLE 26

Ethyl 2-[3-(1-ethyl)piperidyl]thiocarbamoyl-2-(2-pyridyl)acetate

EXAMPLE 27

Ethyl 2-thiocarbamoyl-2-(2-pyridyl)acetate

TABLE 2

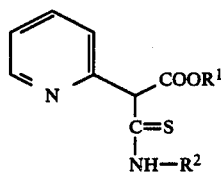

| No. | R¹ | R² | m.p. (°C.) | IR spectrum (cm⁻¹) | NMR spectrum (CDCl₃, δ) | Yield (%) |
|---|---|---|---|---|---|---|
| 17 | CH₃ CH₃ CH₃ (prenyl chain) | H | 65–66 (colorless needle) | 3300, 2920, 1735, 1590, 1280, 1160, 750 (KBr) | 1.58 (3H, s), 1.63 (3H, s), 1.67 (3H, s), 1.97–2.15 (4H, m), 4.56–4.76 (2H, m), 5.05 (1H, br.s) 5.29 (1H, br.t, J=9.2 Hz), 5.43 (1H, s), 7.27 (1H, t, J=4.0 Hz), 7.47 (1H, d, J=7.9 Hz), 7.72 (1H, t.d, J=7.9 Hz, J=2.0 Hz), 7.92 (1H, br.s), 8.56 (1H, d, J=4.0 Hz), 9.57 (1H, br.s) | 49 |
| 18 | CH₃ CH₃ (prenyl) | H | 79–80 (colo prism) | 3340, 1735, 1590, 1440, 1150, 940, 750 (KBr) | 1.61 (3H, s), 1.64 (3H, s), 1.72 (3H, s), 4.52–4.72 (2H, m), 5.27 (1H, br.t), 5.34 (1H, s), 7.25–7.31 (1H, m), 7.46 (1H, d, J=7.3 Hz), 7.73 (1H, t.d, J=7.9 Hz, J=2.0 Hz), 8.56 (1H, d, J=3.9 Hz), 9.58 (1H, br.s) | 58 |
| 19 | C₂H₅ | —CH₂CH₂CH₃ | oil | 3240, 2980, 1740, 1550, 1290, 1160, 750 (film) | 0.97 (3H, t, J=7.3 Hz), 1.21 (3H, t, J=7.3 Hz), 1.60–1.80 (2H, m), 3.50–3.80 (2H, m), 4.10–4.30 (2H, m), 5.38 (1H, s), 7.20–7.32 (1H, m), 7.45 (1H, d, J=7.9 Hz), 7.72 (1H, t. d, J=7.9 Hz J=2.0 Hz), 10.12 (1H, br.s) | 51 |
| 20 | C₂H₅ | —CH₂CH₂CH₂OH | oil | 3250, 1735, 1550, 1430, 1290, 750 (film) | 1.21 (3H, t, J=7.3 Hz), 1.86–1.95 (2H, m), 2.85 (1H, br.s), 3.60–3.72 (2H, m), 3.73–4.06 (2H, m), 4.08–4.26 (2H, m), 5.38 (1H, s), 7.25–7.33 (1H, m), 7.46 (1H, d, J=7.6 Hz), 7.74 (1H, t.d, J=7.6 Hz), J=2.0 Hz), 8.55 (1H, br, d. J=3.9 Hz), 10.30 (1H, br.s) | 45 |
| 21 | C₂H₅ | —CH(CH₃)—C₆H₅ (S) | 66–69 (colorless prism) | 3230, 2960, 1735, 1540, 1430, 1290, 1020, 750, 695 (KBr) | 1.17, 1.23 (each 3H, t, J=6.9 Hz), 1.52, 1.68 (each 3H, d, J=6.9 Hz), 4.10–4.30 (2H, m), 5.37, 5.38 (each 1H, s), 5.58–5.72 (1H, m), 7.16–7.50 (7H, m), 7.65–7.80 (1H, m), 8.50, 8.57 (each 1H, d, J=4.0 Hz), 10.47 (1H, br.s) | 50 |
| 22 | C₂H₅ | —*CH(CH₃)—C₆H₅ (R) | colorless oil | 3250, 2970, 1735, 1540, 1430, 1290, 1200, 750, 695 (film) | 1.17, 1.22 (each 3H, t, J=6.9 Hz), 1.52, 1.68 (each 3H, d, J=6.9 Hz), 4.10–4.30 (2H, m), 5.37, 5.38 (each 1H, s), 5.82–5.72 (1H, m), 7.16–7.50 (7H, m), 7.65–7.80 (1H, m), 8.50, 8.57 (1H, d, J=4.0 Hz), 10.48 (1H, br.s) | 50 |
| 23 | C₂H₅ | —CH(C₆H₅)₂ | 134 colorless prism | 3170, 2950, 1740, 1550, 1295, 1020, 755 (KBr) | 1.19 (3H, t, J=7.3 Hz), 4.12–4.24 (2H, m), 5.43 (1H, s), 6.77 (1H, d, J=7.9 Hz), 7.10–7.14 (1H, m), 7.21–7.44 (11H, m), 7.71 (1H, t.d, J=7.6 Hz, J=2.0 Hz), 8.48 (1H, d, J=4.9 Hz), 10.91 (1H, br.d, J=7.9 Hz) | 57 |
| 24 | C₂H₅ | —CH₂—(2-pyridyl) | 60–68 (colorless prism) | 3220, 2950, 1740, 1595, 1530, 1440, 1290, 1160, 755 (KBr) | 1.21 (3H, t, J=7.3 Hz), 4.13–4.27 (2H, m), 4.85–5.13 (2H, m), 5.47 (1H, s), 7.18–7.75 (6H, m), 8.59 (2H, br.d, J=4.9 Hz), 10.99 (1H, br.s) | 42 |

TABLE 2-continued

[Structure: pyridine-2-yl-CH(COOR¹)-C(=S)-NH-R²]

| No. | R¹ | R² | m.p. (°C.) | IR spectrum (cm⁻¹) | NMR spectrum (CDCl₃, δ) | Yield (%) |
|---|---|---|---|---|---|---|
| 25 | $C_2H_5$ | -piperidinyl-NCH₂-phenyl | oil | 3250, 2940, 1740, 1540, 1435, 1290, 740 (film) | 1.20 (3H, t, J=7.3 Hz), 1.56–2.78 (8H, m), 3.51 (2H, s), 4.08–4.22 (2H, m), 4.30–4.43 (1H, m), 5.32 (1H, s), 7.20–7.38 (6H, m), 7.42 (1H, d, J=7.9 Hz), 7.71 (1H, t.d, J=7.9 Hz, 2.0 Hz), 8.52 (1H, br.d, J=4.0 Hz), 10.20 (1H, br.s) | 50 |
| 26 | $C_2H_5$ | -cyclohexyl-N-$C_2H_5$ | oil | 3250, 2990, 1740, 1530, 1430, 1150, 1020, 750 (film) | 1.02, 1.10 (each 3H, t, J=7.3 Hz), 1.21, 1.22 (each 3H, t, J=6.9 Hz), 1.40–2.80 (10H, m), 4.07–4.29 (2H, m), 4.56 (1H, br.s), 5.35, 5.36 (each 1H, s), 7.20–7.73 (3H, m), 8.47 (1H, d, J=4.0 Hz), 10.40 (1H, br.s) | 37 |
| 27 | $C_2H_5$ | H | 111–112 | 3300, 3180, 1740, 1635, 1590, 1440, 1290, 1170, 1000, 760 (KBr) | 1.22 (3H, t, J=7.3 Hz), 4.10–4.30 (2H, m), 5.34 (1H, s), 7.23–7.48 (1H, m), 7.47 (1H, d, J=7.9 Hz), 7.73 (1H, t.d, J=7.9 Hz, J=2.0 Hz), 7.80 (1H, br.s), 8.57 (1H, br.d, J=4.0 Hz), 9.60 (1H, br.s) | 43 |

Preparation Example 1

| Formulated components | Parts by weight |
|---|---|
| Compound of Example 17 | 95 |
| Lactose | 25 |
| Crystalline cellulose | 10 |
| Corn starch | 100 |

The above components were formulated into preparations according to a conventional method.

For the pharmocological examination of the compounds of the present invention, the following tests were carried out to confirm the effect of inhibiting gastric acid secretion and the protective effect of gastric mucosa. For the toxicity, the test compound was orally administered to six mice of one group to determine the toxicity ($LD_{50}$) thereof.

Test Methods

1. Action on Gastric Acid Secretion (Shay Rat)

Sprague-Dawley strain male rats weighing 200–240 g were used after being starved for 24 hours (water was given ad libitum). Under ether anesthesia, the abdomen was cut and, after ligation of the pylorus part, then closed, and the rat was starved of both food and water. Four hours later the stomach was removed under ether anesthesia and the gastric juice was collected. The gastric juice collected was centrifuged at 3000 rpm for 10 minutes, the volume of the supernatant was measured, and the acidity was determined by titrating 1 ml of the gastric juice with 0.1 N sodium hydroxide solution to pH 7.0. Further, from the amount of gastric juice and the acidity, the acid output (μEg/4h) was calculated; the percentage of inhibition was determined from the following formula, and the percentage of inhibition versus dose (mg/kg) was then plotted on a semi-logarithmic graph to determine the ED50 value. Each test drug was suspended in physiological saline with a few drops of Tween 80 (available from Nakarai Chemicals Ltd.,) and administered into the duodenum at a proportion of 0.2 ml/100 g-body weight immediately after pylorus ligation.

$$\text{Inhibition (\%)} = \frac{\text{Average acid output of control group} - \text{Average acid output of group administered with test compound}}{\text{Average acid output of control group}} \times 100$$

2. Action on Hydrochloric Acid Plus Ethanol Induced Ulcer

Sprague-Dawley strain male rats weighing 200–240 g were used after starving for 24 hours. To each rat, a 60% ethanolic solution containing 150 mM of hydrochloric acid was administered orally at a volume of 0.5 ml/100 g-body weight, and the stomach was removed under ether anesthesia 1 hour later. Into the stomach, 10 ml of a 2% formalin solution was injected, and further the stomach was then immersed in a 2% formalin solution for 15 minutes to fix the inner and outer wall of the stomach. The stomach was cut open along the greater curvature, and the length of the damage generated at the glandular portion of the stomach was measured, and the sum of the lengths of the damages of gastric mucosa per one rat was defined as the lesion index (mm), which was compared with a control group to calculate the percentage of inhibition according to the formula shown below, and then the percentage of inhibition versus dose (mg/kg) was plotted on a semi-logarithmic graph to determine the $ED_{50}$ value. Each test drug was suspended in physiological saline a few drops of Tween 80 and administered orally 30 minutes before administration of the hydrochloric acid ethanolic solution.

$$\text{Inhibition (\%)} = \frac{\substack{\text{Average} \\ \text{lesion index} \\ \text{of control} \\ \text{group}} - \substack{\text{Average lesion} \\ \text{index of group} \\ \text{administered with} \\ \text{test compound}}}{\text{Average lesion index of control group}} \times 100$$

The results of antisecretory effects of gastric acid and protective effects of the gastric mucosa against HCl-EtOH are as shown in Table 3.

TABLE 3

| Example | $ED_{50}$ (mg/kg i.d.) Action on gastric acid secretion | $ED_{50}$ (mg/kg P.O.) Action on HCl— ethanol ulcer | $LD_{50}$ (mg/kg, P.O.) (in mouse) |
|---|---|---|---|
| 1 | 2.4 | — | — |
| 2 | 4.0 | 6.8 | — |
| 3 | 3.8 | — | — |
| 4 | 15.5 | — | — |
| 6 | 9.3 | 3.4 | >1300 |
| 8 | 12.3 | — | — |
| 9 | 3.5 | 1.1 | — |
| 10 | 4.4 | 7.7 | — |
| 12 | 5.0 | 1.4 | >1300 |
| 14 | 36.0 | 3.7 | — |
| 15 | 5.6 | 0.3 | — |
| 17 | 5.3 | 2.8 | >2000 |
| 18 | 7.8 | 4.5 | — |
| 19 | 3.8 | — | — |
| 20 | — | 2.3 | — |
| 24 | 6.4 | — | — |

3. Anti-Aspirin Ulcer Action

Sprague-Dawley-strain male rats weighing about 220 g were starved for 24 hours, and with pylorus being ligated under ether anesthesia, the test drug was administered into the duodenum. After recovery from ether anesthesia, 150 mg/kg of aspirin (suspended in 1% CMC) was orally administered. Five hours later, the stomach was removed under ether anesthesia, 10 ml of 2% formalin solution was injected into the stomach, and the stomach was then immersed in a 2% formalin solution for about 15 minutes. The stomach was then cut open along the greater curvature and the length of the damage generated at the glandular portion of the stomach was measured under dissecting microscope (×10) and the sum of the lengths per one rat (mm) was defined as the lesion index. The $ED_{50}$ value was calculated as described before.

4. Anti-Indomethacin Ulcer Action

Sprague-Dawley-strain male rats weighing about 200–220 g were starved for 24 hours, and 30 mg/kg of indomethacin (suspended in 1% CMC) was administered subcutaneously. After five hours, the stomach was removed under ether anesthesia, and subsequently the same treatment as in the case of an aspirin ulcer was carried out and the sum of the length (mm) of the damage produced at the glandular portion of the stomach per one rat was defined as lesion index. The test drug was administered 30 minutes before administration of indomethacin. The $ED_{50}$ value was calculated as described before.

5. Anti Stress Ulcer

Sprague-Dawley-strain male rats weighing about 240–260 g were starved for 24 hours, and, 30 minutes after oral administration of the test drug, the rat was placed in a stress cage and stress was loaded by immersing the rat into a water tank maintained at 23° C. to the xiphisternum of the chest. Five hours later, the stomach was removed under ether anesthesia, the same treatment as in the case of aspirin ulcer was applied, and the sum of the lengths (mm) of the mucosa damage generated at the glandular portion of the stomach was defined as the lesion index. The $ED_{50}$ value was calculated as described before.

6. Anti-Duodenal Ulcer Action

Sprague-Dawley-strain male rats weighing 200–220 g were starved for 24 hours, and indomethacin (suspended in saline with Tween 80) and histamine 2HCl (dissolved in 10% gelatin solution) were administered following the time schedule shown below. Then, under ether anesthesis, stomach and the duodenal part were removed and 2% formalin solution was injected thereinto. Further, they were immersed in 2% formalin solution for about 15 minutes, and then cut open along the greater curvature to the duodenal part, and the number and area (length in the case of linear ulcer) of the mucosa damages generated at the Corpus, Antrum and Duodenum respectively were measured under stereoscopic microscope (×10), and the sum of the area (mm$^2$) per one rat was defined as lesion index. The $ED_{50}$ value was calculated as described before.

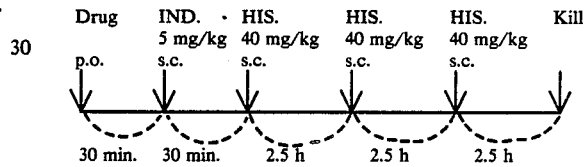

The results of antiulcer effects on various ulcer models and toxicity in rats are shown in Table 4.

TABLE 4

| Example No. | Action on anti-aspirin ulcer | Action on anti-indomethacin ulcer | Action on anti-stress ulcer | Action on anti-duodenal ulcer | $LD_{50}$ (mg/kg, oral) (in rat) |
|---|---|---|---|---|---|
| 12 | 0.8 | 0.7 | 5.3 | 0.6 | — |
| 17 | 1.0 | — | 4.2 | 1.0 | >2856 |

I claim:

1. A 2-pyridylacetic acid derivative having the formula (I):

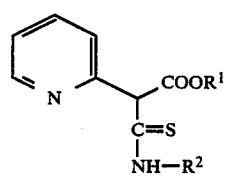

wherein $R^1$ represents an alkyl having 1 to 15 carbon atoms, an alkenyl having 5 to 20 carbon atoms or an aralkyl having 7 to 15 carbon atoms; $R^2$ represents hydrogen, a linear alkyl having 1 to 10 carbon atoms, a cyclic alkyl having 3 to 10 carbon atoms, a hydroxyalkyl having 2 to 6 carbon atoms, an alkenyl having 3 to 6 carbon atoms, an aryl having 6 to 10 carbon atoms, or an aralkyl having 7 to 15 carbon atoms or a pharmacologically acceptable acid addition salt thereof.

2. A compound as claimed in claim 1, wherein said compound is ethyl 2-methylthiocarbamoyl-2-(2-pyridyl)acetate.

3. A compound as claimed in claim 1, wherein said compound is ethyl 2-ethylthiocarbamoyl-2-(2-pyridyl)acetate.

4. A compound as claimed in claim 1, wherein said compound is ethyl 2-allylthiocarbamoyl-2-(2-pyridyl)acetate.

5. A compound as claimed in claim 1, wherein said compound is ethyl 2-cyclohexylthiocarbamoyl-2-(2-pyridyl)acetate.

6. A compound as claimed in claim 1, wherein said compound is ethyl 2-benzylthiocarbamoyl-2-(2-pyridyl)acetate.

7. A compound as claimed in claim 1, wherein said compound is ethyl 2-phenylthiocarbamoyl-2-(2-pyridyl)acetate.

8. A compound as claimed in claim 1, wherein said compound is ethyl 2-adamantylthiocarbamoyl-2-(2-pyridyl)acetate.

9. A compound as claimed in claim 1, wherein said compound is benzyl 2-methylthiocarbamoyl-2-(2-pyridyl)acetate.

10. A compound as claimed in claim 1, wherein said compound is prenyl 2-methylthiocarbamoyl-2-(2-pyridyl)acetate.

11. A compound as claimed in claim 1, wherein said compound is prenyl 2-allylthiocarbamoyl-2-(2-pyridyl)acetate.

12. A compound as claimed in claim 1, wherein said compound is prenyl 2-phenylthiocarbamoyl-2-(2-pyridyl)acetate.

13. A compound as claimed in claim 1, wherein said compound is geranyl 2-methylthiocarbamoyl-2-(2-pyridyl)acetate.

14. A compound a claimed in claim 1, wherein said compound is geranyl 2-allylthiocarbamoyl-2-(2-pyridyl)acetate.

15. A compound as claimed in claim 1, wherein said compound is geranyl 2-phenylthiocarbamoyl-2-(2-pyridyl)acetate.

16. A compound as claimed in claim 1, wherein said compound is farnesyl 2-methylthiocarbamoyl-2-(2-pyridyl)acetate.

17. A compound as claimed in claim 1, wherein said compound is t-butyl 2-methylthiocarbamoyl-2-(2-pyridyl)acetate.

18. A compound as claimed in claim 1, wherein said compound is geranyl 2-thiocarbamoyl-2-(2-pyridyl)acetate.

19. A compound as claimed in claim 1, wherein said compound is prenyl 2-thiocarbamoyl-2-(2-pyridyl)acetate.

20. A compound as claimed in claim 1, wherein said compound is ethyl 2-propylthiocarbamoyl-2-(2-pyridyl)acetate.

21. A compound as claimed in claim 1, wherein said compound is ethyl 2-(3-hydroxypropyl)thiocarbamoyl-2-(2-pyridyl)acetate.

22. A compound as claimed in claim 1, wherein said compound is ethyl 2-[(S)-2-methylbenzyl]thiocarbamoyl-2-(2-pyridyl)acetate.

23. A compound as claimed in claim 1, wherein said compound is ethyl 2-[(R)-2-methylbenzyl]thiocarbamoyl-2-(2-pyridyl)acetate.

24. A compound as claimed in claim 1, wherein said compound is ethyl 2-diphenylmethylthiocarbamoyl-2-(2-pyridyl)acetate.

25. A compound as claimed in claim 1, wherein said compound is ethyl 2-thiocarbamoyl-2-(2-pyridyl)acetate.

26. A peptic ulcer therapeutic composition comprising an effective amount of the 2-pyridylacetic acid derivative as claimed in claim 1, or the pharmacologically acceptable acid addition salt thereof in combination with an inert carrier.

* * * * *